United States Patent [19]

Haefner et al.

[11] Patent Number: 5,690,683

[45] Date of Patent: Nov. 25, 1997

[54] AFTER POTENTIAL REMOVAL IN CARDIAC RHYTHM MANAGEMENT DEVICE

[75] Inventors: Paul A. Haefner, Crystal; Mark A. Stockburger, Inver Grove Heights; William J. Linder, Golden Valley, all of Minn.

[73] Assignee: Cardiac Pacemakers, Inc., St. Paul, Minn.

[21] Appl. No.: 492,199

[22] Filed: Jun. 19, 1995

[51] Int. Cl.$^6$ ............................................. A61N 1/39
[52] U.S. Cl. .................... 607/4; 607/5; 607/13; 128/696; 128/901
[58] Field of Search ............ 607/5, 4, 13; 128/696, 128/901

[56] References Cited

U.S. PATENT DOCUMENTS

| | | | |
|---|---|---|---|
| 3,569,852 | 3/1971 | Berkovits | 128/901 |
| 4,170,999 | 10/1979 | Allen et al. | 607/13 |
| 4,498,478 | 2/1985 | Bourgeois | 607/13 |
| 4,677,986 | 7/1987 | DeCote, Jr. | 128/901 |
| 5,024,221 | 6/1991 | Morgan | 128/419 |
| 5,117,824 | 6/1992 | Keimel et al. | 607/4 |
| 5,330,504 | 7/1994 | Sommerville et al. | 607/5 |
| 5,350,404 | 9/1994 | Adams et al. | 607/5 |
| 5,376,104 | 12/1994 | Sakai et al. | 607/5 |
| 5,470,342 | 11/1995 | Mann et al. | 607/4 |

FOREIGN PATENT DOCUMENTS

| | | |
|---|---|---|
| 0011932 | 6/1980 | European Pat. Off. . |
| 0344878 | 12/1989 | European Pat. Off. . |
| 0605264 | 7/1994 | European Pat. Off. . |

Primary Examiner—William E. Kamm
Assistant Examiner—Kennedy J. Schaetzle
Attorney, Agent, or Firm—Schwegman, Lundberg, Woessner & Kluth, P.A.

[57] ABSTRACT

An apparatus effectively removes after potential occurring after a electrical pulse is delivered in a cardiac rhythm management system such as a pacemaker system or cardioverter/defibrillator system having an electrode used for both sensing electrical activity of the heart and carrying the electrical pulse to the heart and a sense amplifier for detecting the electrical activity from the electrode. The apparatus includes a lowpass filter coupled to the electrode to filter the sensed electrical activity. A highpass filter is coupled between the lowpass filter and the sense amplifier to further filter the electrical activity passed from the lowpass filter. Equilibrium circuitry is included to allow passive filter components of the lowpass filter and the highpass filter to return to an equilibrium state following delivery of the electrical pulse.

43 Claims, 3 Drawing Sheets

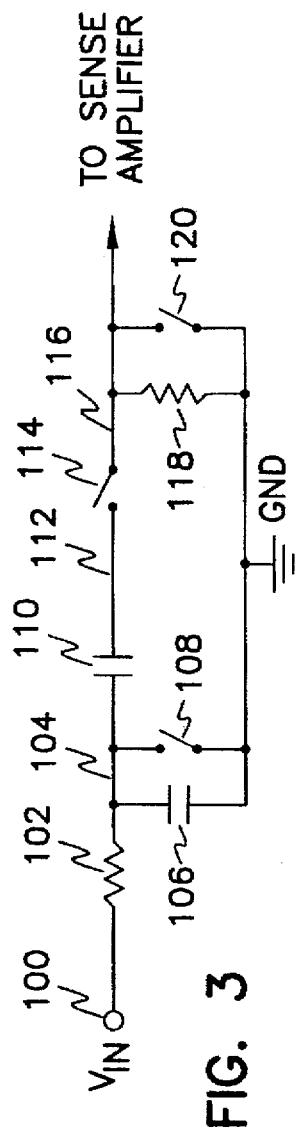
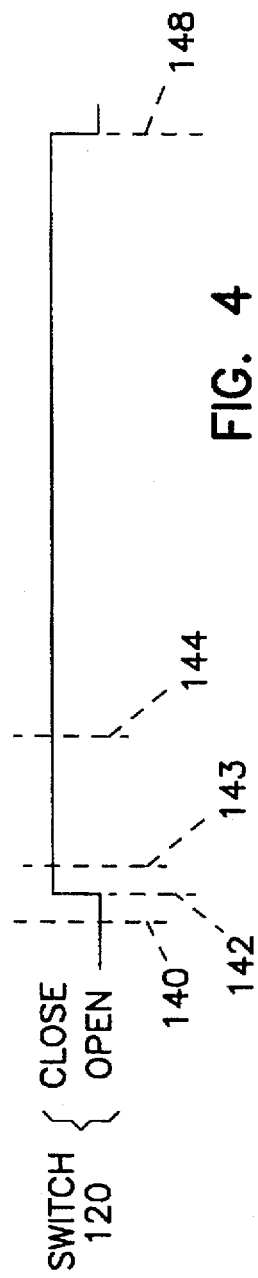
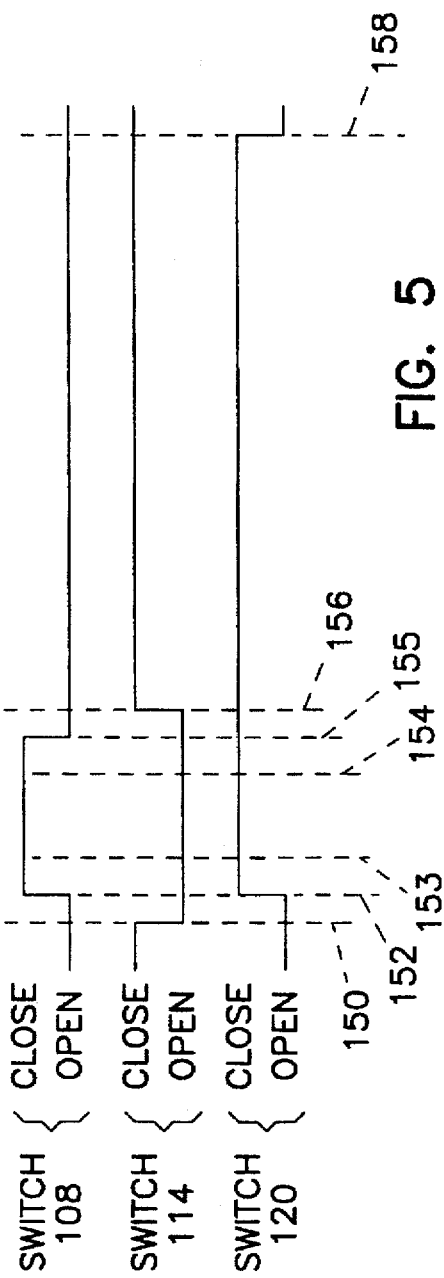

AFTER POTENTIAL REMOVAL IN CARDIAC RHYTHM MANAGEMENT DEVICE

FIELD OF THE INVENTION

The present invention generally relates to implantable medical devices, and more particularly, to after potential removal circuitry for a cardiac rhythm management device such as a cardiac pacemaker and/or cardioverter/defibrillator.

BACKGROUND OF THE INVENTION

Cardiac rhythm management systems include leads or electrodes disposed in at least one of the chambers of the heart to sense electrical activity occurring in the chamber. For example, leads disposed in the atrial chamber of the heart sense electrical activity representative of a P-wave portion of the PQRST complex of a surface electrogram (EGM) indicating depolarizations in the atrium or leads disposed in the ventricular chamber of the heart sense electrical activity representative of a R-wave portion of the PQRST complex of a surface EGM indicating depolarizations in the ventricle. An implantable cardiac rhythm management system also includes a pulse generator device, such as a cardiac pacemaker, a cardioverter/defibrillator, or a cardioverter/defibrillator with pacing capability, used to treat certain arrhythmia conditions in the heart such as bradycardia and tachyarrhythmia (including ventricular fibrillation and ventricular tachycardia) based on the sensed electrical activity. There are a variety of well known methods and apparatus for detecting, analyzing, and storing depolarization information related to the sensed electrical activity of the heart for the purpose of detecting and treating arrhythmia conditions with implantable cardiac rhythm management systems.

Present cardiac pacemakers and cardioverter/defibrillators create after-potentials following a pacing pulse or shock pulse which are much greater than the invoked potentials of the myocardium. As a result, immediate detection of depolarizations in the heart is very difficult, if not impossible, due to the after-potential effect. Prior systems have attempted to reduce the effects of such after-potentials by various methods.

One such method utilized in some cardiac rhythm management systems is to use separate leads or electrodes for pulse delivery and sensing. In fact, some cardioverter/defibrillator systems with pacing capability use separate leads for pacing, shock delivery, and sensing. However, surgical procedures for implanting cardiac rhythm management systems are much more complex with the extra leads required to have separate electrodes for pulse delivery and sensing. In addition, the extra electrodes tend to produce additional failures in the implanted system.

Other cardiac rhythm management systems deliver a pulse to the heart and sense on the same leads or electrodes. Some cardioverter/defibrillator systems with pacing capability pace, deliver high energy shock pulses, and sense through the same electrodes. When the same electrodes are used to deliver a pulse to the heart and for sensing, a standard practice in the art is to blank for many milliseconds the sense amplifier connected to the lead over which the pacing pulse or shock pulse is generated. There have been many attempts to shorten the blanking periods by speeding up the charge dissipation process of the after potential.

SUMMARY OF THE INVENTION

The present invention provides a cardiac rhythm management pulse generator device for generating electrical pulses. The pulse generator device is coupleable to an electrode which senses electrical activity of the heart and carries the electrical pulses to the heart. The pulse generator device includes an input/output terminal connectable to the electrode to receive the electrical activity from the electrode and to provide the electrical pulses to the electrode. A lowpass filter is coupled to the input/output terminal and filters the sensed electrical activity. A highpass filter is coupled to the lowpass filter for further filtering the electrical activity passed from the lowpass filter. The highpass filter includes a resistive portion coupled to a ground node. A switch is operable to effectively remove the resistive portion from the highpass filter. A sense amplifier is coupled to the highpass filter for amplifying the electrical activity of the heart passed from the highpass filter. A cardiac depolarization detector is coupled to the sense amplifier and detects cardiac depolarizations in the amplified electrical activity of the heart to provide a depolarization signal indicative of the depolarizations. A pulse circuit is coupled to the input/output terminal and the cardiac depolarization detector for generating the electrical pulses based on the depolarization signal.

The cardiac rhythm management pulse generator device of the present invention can be embodied in a pacemaker, a cardioverter/defibrillator, or a cardioverter/defibrillator with pacing capability. In any of these embodiments, the pulse generator device preferably includes a switch controller such as a microprocessor and/or state machine for operating the switch to effectively remove the resistive portion from the highpass filter for a selected period of time following an electrical pulse provided by the pulse circuit. The removal of the resistive portion from the highpass filter permits passive filter components of the lowpass filter and the highpass filter to return more quickly to an equilibrium state following the delivery of the electrical pulse.

When the cardiac rhythm management pulse generator device is embodied in a cardioverter/defibrillator, the cardioverter/defibrillator includes a second switch preferably controlled by the switch controller to disconnect the sense amplifier from the highpass filter prior to a shock pulse being generated by the cardioverter/defibrillator. In this way, the sense amplifier and other sensing circuitry is protected from the shock pulse.

The lowpass filter of the pulse generator device according to the present invention preferably includes a capacitor coupled to the ground node. When the pulse generator device is embodied in a cardioverter/defibrillator, a third switch is preferably included to be operable under microprocessor and/or state machine control to effectively remove the capacitor from the lowpass filter for a selected period of time ranging from before each shock pulse is generated by the cardioverter/defibrillator until after each shock pulse dissipates. In this way, a shock current created by the after potential caused by the delivery of each shock pulse is bypassed through the ground node.

When the cardiac rhythm management system of the present invention is embodied in a pacemaker, the pacemaker preferably does not include disconnecting circuitry such as the above-described second switch for disconnecting the sense amplifier from the highpass filter prior to the delivery of a shock pulse in a cardioverter/defibrillator system. The disconnecting circuitry is not needed with the present invention because of the effects of the combined lowpass and highpass filters and the switch for effectively removing the resistor portion from the highpass filter for the selected period of time following a pacing pulse provided by the pacemaker.

When the cardiac rhythm management system is embodied in a cardioverter/defibrillator with pacing capability, the three above-described switches are controlled differently under microprocessor and/or state machine control based on if the cardioverter/defibrillator is pacing or providing a shock pulse. When delivering a shock pulse, the three switches operate as described above for the cardioverter/ defibrillator embodiment. When delivering pacing pulses, the first switch operates as above to remove the resistive portion for a selected period of time following the pacing pulse. However, when providing the pacing pulse, the system effectively removes the after potential occurring after a pacing pulse is delivered with the second switch operated to connect the sense amplifier to the highpass filter during the entire pacing cycle, and with the third switch operated to keep the capacitor in the lowpass filter during the entire pacing cycle.

BRIEF DESCRIPTION OF THE DRAWINGS

FIG. 3 is a schematic diagram of filter and after potential removal circuitry according to the present invention.

FIG. 4 is a timing diagram illustrating the operation of switches in the circuitry of FIG. 3 operating under pacing conditions.

FIG. 5 is a timing diagram illustrating the operation of switches in the circuitry of FIG. 3 operating under cardioverter/defibrillator conditions.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
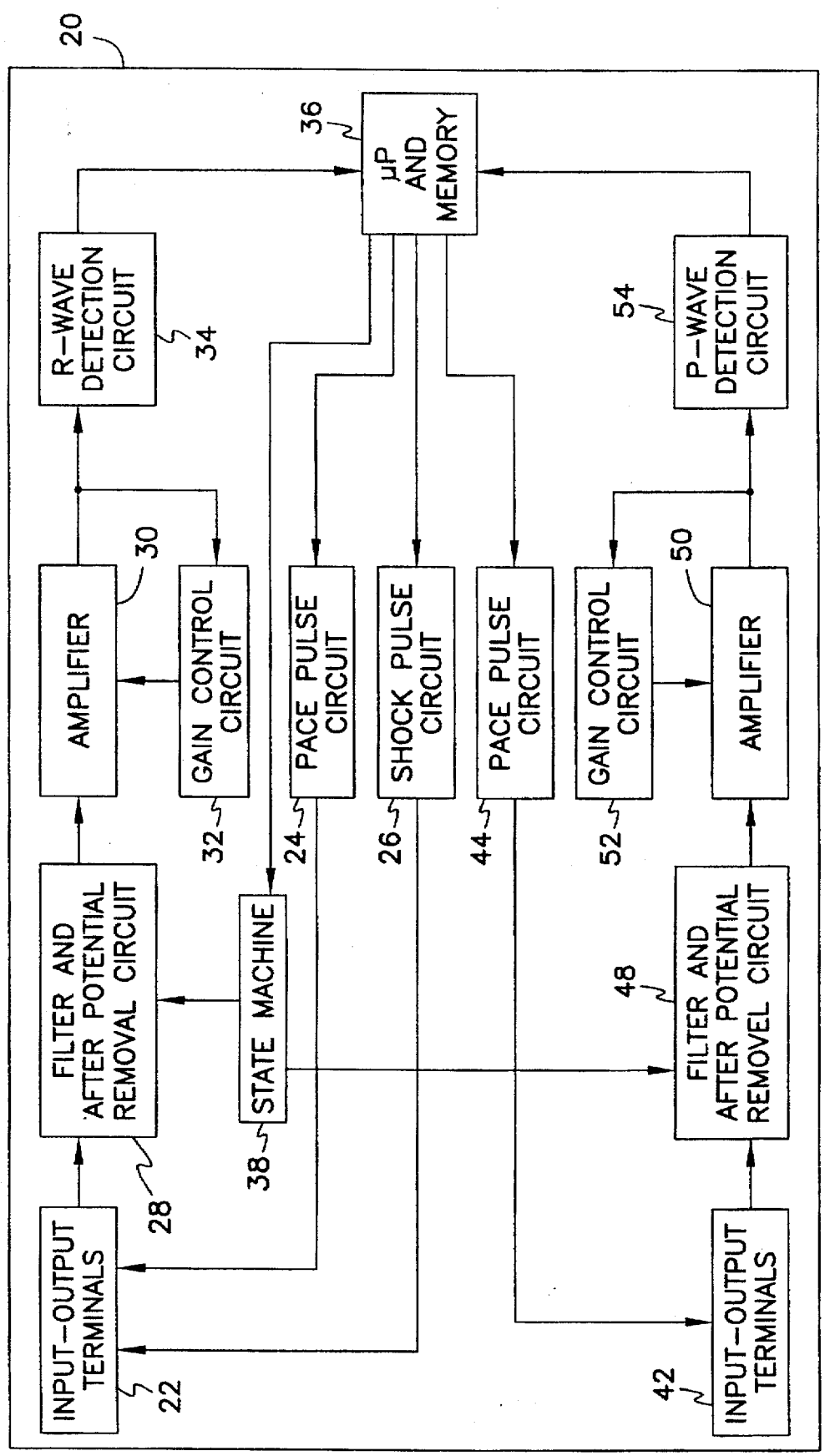
FIG. 1 is a block diagram of a cardioverter/defibrillator with pacing capability according to the present invention.

A dual chamber cardioverter/defibrillator 20 with pacing capability is illustrated in block diagram form in FIG. 1. Cardioverter/defibrillator 20 operates as a pulse generator device portion of a cardiac rhythm management system which also includes leads or electrodes (not shown) disposed in the ventricular chamber of the heart to sense electrical activity representative of a R-wave portion of the PQRST complex of a surface EGM indicating depolarizations in the ventricle. Cardioverter/defibrillator 20 includes input/output terminals 22 which are connectable to the ventricular leads to receive the ventricular electrical activity of the heart sensed by the ventricular leads. A pace pulse circuit 24 provides pacing pulses such as bradycardia and antitachycardia pacing pulses to input/output terminals 22 to be provided to the ventricular chamber of the heart via the ventricular leads to stimulate excitable myocardial tissue to treat arrhythmia conditions such as bradycardia and some tachycardia. A shock pulse circuit 26 provides shock pulses to input/output terminals 22 to be provided to the ventricular chamber of the heart via the ventricular leads to shock excitable myocardial tissue to treat tachyarrhythmia conditions. The tachyarrhythmia conditions may include either ventricle fibrillation or ventricle tachycardia.

A filter and after potential removal circuit 28 according to the present invention filters the ventricular electrical activity received by input/output terminals 22 and the pacing pulses provided from pacing pulse circuit 24. In addition, filter and after potential removal circuit 28 effectively removes after potential created by a pacing pulse from pacing pulse circuit 24 or a shock pulse delivered by shock pulse circuit 26. An amplifier 30 amplifies the filtered ventricular electrical activity provided from the filter and after potential removal circuit 28. A gain control circuit 32 automatically adjusts the gain of amplifier 30. Amplifier 30 and gain control circuit 32 can be implemented in any well known automatic gain control circuit. An R-wave detection circuit 34 is coupled to amplifier 30 to detect depolarizations in the amplified ventricular electrical activity representative of R-wave depolarizations. Amplifier 30 preferably includes circuitry for digitizing the ventricular electrical activity data for detection by R-wave detection circuit 34.

R-wave detection circuit 34 provides a R-wave depolarization signal, indicative of the R-wave depolarizations, to a microprocessor and memory 36. Microprocessor and memory 36 operates using any well known algorithm for detection of arrhythmia conditions. For example, microprocessor and memory 36 can be used to analyze the occurrence of detected R-waves including the rate, regularity, and onset of variations in the rate of the reoccurrence of the detected R-wave, the morphology of the detected R-wave, or the direction of propagation of the depolarization represented by the R-wave in the heart. In addition, microprocessor and memory 36 stores R-wave data and uses known techniques for analysis of the detected R-waves for controlling pace pulse circuit 24 and shock pulse circuit 26 for delivery of pace pulses and shock pulses, respectively. In addition, microprocessor and memory 36 controls a state machine 38. State machine 38 places corresponding circuits of cardioverter/defibrillator 20 including filter and after potential removal circuit 28 in desired logic states as dictated by the microprocessor and memory 36 based on various conditions such as when a pace pulse or a shock pulse occurs.

The cardiac rhythm management system also includes leads or electrodes (not shown) disposed in the atrial chamber of the heart to sense electrical activity representative of a P-wave portion of the PQRST complex of a surface EGM indicating depolarizations in the atrium. Cardioverter/ defibrillator 20 correspondingly also includes input/output terminals 42 which are connectable to the atrial leads to receive the atrial electrical activity of the heart sensed by the atrial leads. A pace pulse circuit 44 provides pacing pulses such as bradycardia pacing pulses to input/output terminals 42 to be provided to the atrial chamber of the heart via the atrial leads to stimulate excitable myocardial tissue to treat arrhythmia conditions such as bradycardia. A filter and after potential removal circuit 48 operates similar to filter and after potential removal circuit 28 to filter the atrial electrical activity received by input/output terminals 42 and the pacing pulses provided from pacing pulse circuit 44. In addition, filter and after potential removal circuit 48 effectively removes after potential created by a pacing pulse from pacing pulse circuit 44.

An amplifier 50 amplifies the filtered atrial electrical activity provided from filter and after potential removal circuit 48. A gain control circuit 52 automatically adjusts the gain of amplifier 50. Gain control circuit 52 and amplifier 50 operate similar to gain control 32 and amplifier 30. A P-wave detection circuit 54 is coupled to amplifier 50 to detect depolarizations in the amplified atrial electrical activity representative of P-wave depolarizations. Amplifier 50 preferably includes circuitry for digitizing the atrial electrical activity data for detection by P-wave detection circuit 54.

P-wave detection circuit 54 provides a P-wave depolarization signal, indicative of the P-wave depolarizations, to microprocessor and memory 36. Microprocessor and memory 36 analyzes the detected P-waves indicated in the P-wave depolarization signal from P-wave detection circuit 54 along with the R-wave depolarization signal provided from R-wave detection circuit 34 for the detection of arrhythmia conditions based on known algorithms. For example, microprocessor and memory 36 can be used to analyze the rate, regularity, and onset of variations in the rate of the reoccurrence of the detected P-wave and R-wave, the morphology of the detected P-wave and R-wave, or the direction of propagation of the depolarization represented by the detected P-wave and R-wave in the heart. In addition, microprocessor and memory 36 stores P-wave data and uses known techniques for analysis of the detected P-waves to control pace pulse circuit 44 for proper delivery of pace pulses to the atrium. In addition, microprocessor and memory 36 controls a state machine 38 which places filter and after potential removal circuit 48 in desired logical states based on various conditions such as when a pace pulse to the atrium occurs.

The dual chamber cardioverter/defibrillator 20 with pacing capability illustrated in FIG. 1 includes pacing and shocking capabilities for the ventricle and pacing capability for the atrium. Nevertheless, the present invention can be embodied in a single chamber cardiac rhythm management device having a single one of these capabilities. For example, the present invention can be embodied in a ventricle defibrillator device for providing shock pulses to the ventricle only or in a cardiac pacemaker device for providing pace pulses to the ventricle only.

Input/output terminals 22 and 42 are typically implemented to be connectable to a single set of electrodes (not shown) used for pacing, shock delivery, and sensing. The electrodes of a cardiac rhythm management system are typically implemented as unipolar or bipolar electrodes.

A unipolar electrode configuration has one pole or electrode (i.e., negative pole or cathode electrode) located on or within the heart, and the other pole or electrode (i.e., positive pole or anode electrode) remotely located from the heart. With endocardial leads, for example, the cathode is located at the distal end of a lead and typically in direct contact with the endocardial tissue to be stimulated, thus forming a "tip" electrode. Conversely, the anode is remotely located from the heart, such as comprising a portion of the metallic enclosure which surrounds the implanted device, thus forming a "can" electrode and is often referred to as the "indifferent" electrode.

A bipolar electrode configuration has both poles or electrodes typically located within the atrial or ventricular chamber of the heart. With endocardial leads, for example, the cathode is located at the distal end of the lead, referred to as the "tip" electrode. In the bipolar configuration, the anode is usually located approximate to the "tip" electrode spaced apart by 0.5 to 2.5 cm., and typically forming a ring-like structure, referred to as the "ring" electrode.

With respect to sensing, it is well known that bipolar and unipolar electrode configurations do not yield equivalent cardiac EGMs. Each configuration has advantages and disadvantages, for example, with a unipolar-sensing configuration, only the electrical events adjacent to the "tip" electrode control the unipolar EGM, while the remote "indifferent" electrode contributes negligble voltage due to its location being extracardiac.

With a bipolar-sensing configuration, the magnitude of the cardiac signal is similar for both the "ring" and the "tip" electrodes, but the resulting EGM is highly dependent upon the orientation of the electrodes within the heart. Optimal sensing will occur, for example, when the sensing vector defined by the sensing electrodes is parallel with the dipole defined by the depolarization signal. Since bipolar electrodes are more closely spaced than their unipolar counterparts, the depolarization signal will be shorter in duration than that produced from a unipolar configuration. Due to a more restrictive lead field or antenna, bipolar sensing offers improved rejection of electromagnetic and skeletal muscle artifacts, and thus provides a better signal-to-noise ratio than unipolar sensing.

When either unipolar or bipolar electrodes are used for both sensing and delivery of the pacing or shock pulse, detection of the depolarization is typically reduced, because the detection is masked or buried in the exponential decay of the after potential or residual polarization charge on the electrode resulting from the stimulation pulse itself. Thus, until the charges resulting from the pacing or shock stimulus dissipates sufficiently, reliable sensing is impossible because the potentials arising from the after potential charges are so much greater than those resulting from a heart beat.

Figure 2:
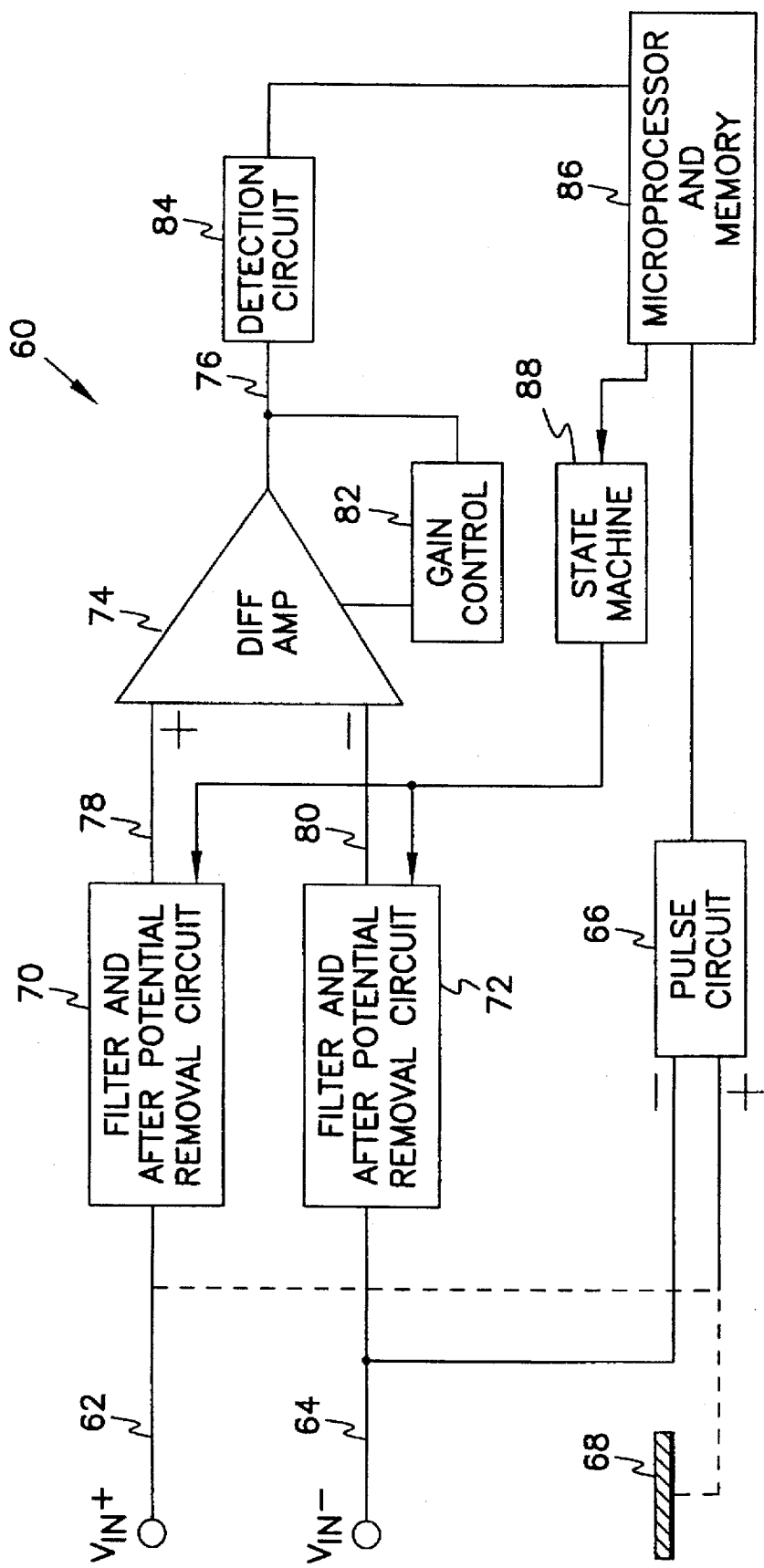
FIG. 2 is a schematic block diagram of a cardiac rhythm management system according to the present invention.

A block and schematic diagram of the relevant portions of a cardiac rhythm management system according to the present invention comprising bipolar sensing leads or electrodes for sensing electrical activity from either the atrial or ventricle chamber of the heart is illustrated generally at 60 in FIG. 2. Cardiac rhythm management system 60 can be embodied in a pacemaker system, cardioverter/defibrillator system, or cardioverter/defibrillator system with pacing capability.

Cardiac rhythm management system 60 includes a positive bipolar electrode 62 and a negative bipolar electrode 64 for sensing positive and negative electrical activity respectively from either the atrium or the ventricle. Bipolar electrodes 62 and 64 may advantageously be a tip electrode and a ring electrode as is typically used in a pacemaker device In addition, a pulse circuit 66 delivers electrical pulses such as pacing pulses or shock pulses for treatment of arrhythmia conditions via a negative output to negative bipolar electrode 64. In a pacemaker system embodiment of cardiac rhythm management system 60, a positive output of pulse generator 66 is connected to positive bipolar electrode 62 to provide a completion path for the pace pulse. In a cardioverter/defibrillator system embodiment of cardiac rhythm management system 60, the positive output of pulse generator 66 is connected to an indifferent electrode 68 instead of positive bipolar electrode 62. Indifferent electrode 68 provides a completion path for the delivery of the electrical shock potential to body tissue from pulse circuit 66. Indifferent electrode 68 can be a bipolar ring or other current path such as a defibrillator shocking lead, patch electrode, or can electrode in the cardioverter/defibrillator system embodiment. Such patch electrodes are well known in the art.

A filter and after potential removal circuit 70 functions to filter the positive electrical activity sensed by positive electrode 62. In addition, filter and after potential circuit 70 effectively removes after potential caused by a electrical pulse delivered by pulse circuit 66. A filter and after potential removal circuit 72 operates similar to filter and after potential removal circuit 70 to filter the negative electrical activity sensed by negative electrode 64 in addition to effectively removing the after potential effects of a electrical pulse delivered from pulse circuit 66.

A differential amplifier 74 senses and amplifies the difference between the filtered positive electrical activity provided from filter and after potential removal circuit 70 on a line 78 and the filtered negative electrical activity provided from filter and after potential removal circuit 72 on a line 80. The reactive surface areas of bipolar electrodes 62 and 64 are preferably empirically optimized based on a variety of parameters such as pacing threshold requirements, sensing impedance requirements, defibrillator threshold requirements, and increasing the differential between the signals on lines 78 and 80 for sensing by differential amplifier 74. The after potential created on each electrode is not predictable or repeatable and varies due to various factors such as the reactive surface area of the electrode, the possibly differing reactive surface areas of bipolar electrodes, electrode position and orientation in relation to the heart, and the material and physical structure of the electrode.

Differential amplifier 74 provides a differential amplified output signal on a line 76 representing the difference between the signals appearing on line 78 and line 80. Differential amplifier 74 can be any suitable differential amplifier as is conventionally available in the art. A gain control circuit 82 adjusts a gain of differential amplifier 74. A detect circuit 84 detects either P-wave depolarizations or R-wave depolarizations in the differential amplified output signal provided on line 76. Differential amplifier 74 preferably includes circuitry for digitizing the electrical activity data to provide a digitized signal on line 76 to detect circuit 84.

Detection circuit 84 provides a depolarization signal, indicative of the P-wave or R-wave depolarizations, to a microprocessor and memory 86. Microprocessor and memory 86 analyzes the detected depolarizations indicated in the depolarization signal from detection circuit 84 for the detection of arrhythmia conditions based on known algorithms. For example, microprocessor and memory 86 can be used to analyze the rate, regularity, and onset of variations in the rate of the reoccurrence of the detected depolarization, the morphology of the detected depolarization, or the direction of propagation of the depolarization. In addition, microprocessor and memory 86 stores depolarization data and uses known techniques for analysis of the detected depolarizations to control pulse circuit 66 for proper delivery of electrical pulses to the atrium or the ventricle. Microprocessor and memory 86 also controls a state machine 88. State machine 88 places corresponding circuits of cardiac rhythm management system 60 including filter and after potential removal circuits 70 and 72 in desired logic states as dictated by microprocessor and memory 86 based on various conditions such as when an electrical pulse to the heart occurs.

FIG. 3 illustrates in a schematic diagram form the filter and after potential removal circuit according to the present invention, such as the filter and after potential removal circuits 28 and 48 of FIG. 1 or the filter and after potential removal circuits 70 and 72 of FIG. 2.

Referring to FIG. 3, an input terminal 100 receives the input voltage (VIN) representing the received electrical activity and the pacing or shock pulses provided from the input/output terminals, such as input/output terminals 22 or 42 of FIG. 1, or, as schematically illustrated in FIG. 2, from one of the bipolar electrodes 62 or 64. A resistor 102 includes a first terminal coupled to input terminal 100 and a second terminal coupled to a node 104. A capacitor 106 includes a first terminal coupled to node 104 and a second terminal coupled to a ground node. A switch 108 includes a first terminal coupled to node 104 and a second terminal coupled to the ground node. A capacitor 110 includes a first terminal coupled to node 104 and a second terminal coupled to a node 112. A switch 114 includes a first terminal coupled to node 112 and a second terminal coupled to a node 116. A resistor 118 includes a first terminal coupled to node 116 and a second terminal coupled to the ground node. A switch 120 includes a first terminal coupled to node 116 and a second terminal coupled to the ground node. Node 116 is coupled to the input of the sense amplifier of the cardiac rhythm management pulse generator device such as amplifier 30 or 50 of FIG. 1 or one of the inputs of differential amplifier 74 of FIG. 2.

When switch 108 is open, resistor 102 and capacitor 106 operate together as a lowpass filter. When switch 114 is closed and switch 120 is open, capacitor 110 and resistor 118 operate together as a highpass filter. Thus, when switch 108 is open, switch 114 is closed, and switch 120 is open, the combination of the lowpass filter comprising resistor 102 and capacitor 106 and the highpass filter comprising capacitor 110 and resistor 118 operate together as a bandpass filter to filter the sensed electrical activity from either the atrium or ventricle.

Although switches 108, 114, and 120 are schematically illustrated for clarity as mechanical switching devices, switches 108, 114, and 120 are preferably implemented as electronic switches, such as field effect transistors (FETS) having low ON resistance characteristics or equivalent solid state switching devices.

When operating under pacing conditions, switch 108 preferably remains open and switch 114 preferably remains closed throughout the entire pacing cycle. The operation of switch 120 under pacing conditions, as controlled by the microprocessor and/or state machine of the pacing device, such as microprocessor and memory 36 and state machine 38 of FIG. 1 or microprocessor and memory 86 and state machine 88 of FIG. 2, is illustrated in timing diagram form in FIG. 4. As is illustrated in FIG. 4, a pace command is issued by the microprocessor at time 140. Prior to the pace command being issued, switch 120 is open. At time 142, approximately one synchronization pulse after the pace command is issued by the microprocessor, switch 120 is closed to connect node 116 to the ground node. By shorting node 116 to ground, switch 120 effectively removes resistor 118 from the highpass filter and also increases the RC time constant of the lowpass filter. At time 143, approximately one synchronization pulse after switch 120 is closed, the pace pulse circuit provides the pace pulse to the input/output terminals.

The time indicated at 144 represents the end of the pacing recharge cycle. At time 148, switch 120 is opened through microprocessor and state machine control. The time between the time indicated at 144 and the time indicated at 148 preferably represents approximately seven filter time constants in order to allow passive filter components including capacitor 106 of the lowpass filter and capacitor 110 of the highpass filter to return to an equilibrium state. The preferred approximately seven filter time constants minimize the size of transients thrown into the sense amplifier as a result of the after potential created from a pacing pulse. Thus, the sense amplifier settling time is minimized to enable fast recovery times, which results in more reliable sensing of actual P-wave or R-wave depolarizations.

Unlike previous after potential removal circuitry designs, the after potential removal circuitry of the present invention prevents saturation of the sense amplifier and tracking of a pacing pulse without disconnecting the sense amplifier inputs even when the same electrode is used for both sensing and pacing.

FIG. 5 illustrates in timing diagram form the operation of switches 108, 114, and 120, when the cardiac rhythm management system according to the present invention is operating under cardioverter/defibrillator conditions. The operation of switches 108, 114, and 120 is controlled by the microprocessor and/or state machine of the cardioverter/defibrillator device, such as microprocessor and memory 36 and state machine 38 of FIG. 1 or microprocessor and memory 86 and state machine 88 of FIG. 2. Prior to a shock delivery command being issued by the microprocessor, switch 108 is open, switch 114 is closed, and switch 120 is open. At time 150, shock delivery command is issued by the microprocessor and switch 114 is opened to disconnect the amplifier inputs to prevent saturation of the sense amplifier and to protect the amplifier and other sensing circuitry. At time 152, approximately one synchronization pulse after the shock delivery command is issued, switch 108 is closed to connect node 104 to the ground node. By shorting node 104 to ground, capacitor 106 is effectively removed from the lowpass filter to permit bypass of the shock current created by a shock pulse through the ground node. Thus, switch 108 is closed to serve as a clamping device to limit the charge in capacitor 106 resulting from the delivery of a shock pulse. Also at time 152, switch 120 is closed to connect node 116 to the ground node to effectively remove resistor 118 from the highpass filter. At time 153, approximately one synchronization pulse after switches 108 and 120 are closed a high voltage electrical shock pulse is provided to the input/output terminals to be provided to the ventricle channel of the heart.

The time indicated at 154 represents the end of the shocking pulse. At time 155, approximately one synchronization pulse after the time indicated at 154, switch 108 is opened to effectively reconnect capacitor 106 between node 104 and the ground node to complete the lowpass filter. At time 156, approximately one synchronization pulse after switch 108 is opened, switch 114 is closed to end the disconnecting period by connecting capacitor 110 to node 116 to again allow sensing of the electrical activity by the sense amplifier.

At time 158, switch 120 is opened to effectively reconnect resistor 118 to the highpass filter. The time represented between time 156 and time 158 preferably represents approximately seven filter time constants to allow the passive filter components including capacitor 106 of the lowpass filter and capacitor 110 of the highpass filter to return to an equilibrium state. The preferred approximately seven filter time constants minimize the size of the transients thrown into the sense amplifier as a result of the after potential created from the delivery of a shock pulse. Thus, the sense amplifier settling time is minimized to permit fast recovery times, which results in more reliable sensing of actual R-wave and/or P-wave depolarizations in a cardiac rhythm management system. It is especially useful in a cardioverter/defibrillator system having pacing capability to reduce transients in the sense amplifier to permit chamber sensing for possible pacing conditions soon after the delivery of a shock pulse.

The filter and after potential removal circuit according to the present invention effectively reduces the capacitive effect of the after potential resulting from a shock delivery so that R-wave and/or P-wave sensing is resumed as quickly as possible after delivery of the shock pulse. In addition, the lowpass filter comprising resistor 102 and capacitor 106 effectively slows down transients. Moreover, the highpass filter comprising capacitor 110 and resistor 118 substantially eliminates slowly changing fluctuations in the incoming signal to the sense amplifier.

Three design criteria are preferably used to design the passive RC bandpass filter network. First, a lowpass filter pole frequency is preferably set based on antialias filter requirements, because the RC bandpass filter preferably operates ahead of a sampled filter network for conversion of the input electrical analog waveform into digital form. The lowpass filter is used to attenuate unwanted high frequencies within the signal or accompanying noise on the input channel which cause aliasing. Thus, the lowpass pole is set based on a filter sampling rate and expected noise frequencies.

The second design criteria is the setting of the highpass pole frequency. The highpass pole frequency is set as high as possible while still ensuring overall channel filter characteristics. If the highpass filter pole frequency is set too low, the post shock delay time is increased along with an increase in the channel amplifier settling time.

The third design criteria of the passive RC bandpass filter network is the resistor ratio between resistor 102 and resistor 118. The resistor ratio is adjusted to minimize attenuation of the incoming electrical signal without significantly lowering the highpass frequency pole. If the attenuation is minimized, the incoming electrical signal is kept as large as possible. With the larger electrical input signal, noise affects on the input signal are significantly reduced. In the preferred embodiment of the present invention, the attenuation is set to approximately 0.8, because the resistance values need to be set to reasonable values without causing tolerance problems.

An example of suitable values for the components of the RC filter network are as follows: resistor 102 approximately equal to 200K ohms; capacitor 106 approximately equal to 2700 pF; capacitor 110 approximately equal to 0.014 µF; and resistor 118 approximately equal to 1M ohm. Of course, the circuitry of the cardiac rhythm management system coupled to the filter and after potential removal circuit can affect the design criteria for picking the RC component values. As is known in the art, many values could be substituted for the RC filter components to meet the above design criteria to effectively remove the after potential occurring after either a shock pulse or a pacing pulse according to the present invention.

The filter and after potential removal circuitry of the present invention effectively removes the after potential occurring after a shock pulse or pacing pulse is delivered in an implantable cardiac rhythm management system which has an electrode for sensing and delivery of the voltage pulses. In fact, in a cardioverter/defibrillator system with pacing capability, the pacing pulse, the shock pulse, and the sensed data are preferably all provided on the same electrode or electrodes. Surgical procedures for implanting a cardiac rhythm management system is greatly simplified by having one set of leads for pulse delivery and sensing. Thus, the time and cost to implant a cardiac rhythm management system having a single lead set is much less than a system having separate lead sets for sensing and pulse delivery. In addition, the reduced electrodes or leads tends to reduce the amount of failures occurring in an implanted cardiac rhythm management system.

What we claim is:

1. A cardiac rhythm management pulse generator device for generating electric pulses and coupleable to an electrode which senses electrical activity of the heart and carries the electrical pulses to the heart, the pulse generator device comprising:

an input/output terminal connectable to the electrode to receive the sensed electrical activity of the heart from the electrode and provide the electrical pulses to the electrode;

a lowpass filter coupled to the input/output terminal for filtering the sensed electrical activity;

a highpass filter coupled to the lowpass filter for further filtering the electrical activity passed from the lowpass filter, the highpass filter including a resistive portion coupled to a ground node;

a switch operable to effectively remove the resistive portion from the highpass filter;

a sense amplifier coupled to the highpass filter for amplifying the electrical activity of the heart passed from the highpass filter;

a cardiac depolarization detector coupled to the sense amplifier for detecting depolarizations in the amplified electrical activity of the heart and providing a depolarization signal indicative of the depolarizations; and a pulse circuit coupled to the input/output terminal and the cardiac depolarization detector for generating the electrical pulses based on the depolarization signal.

2. The pulse generator device of claim 1 further comprising control means for operating the switch to effectively remove the resistive portion for a selected period of time following each electrical pulse generated by the pulse circuit.

3. The pulse generator device of claim 1 wherein the pulse circuit generates pacing pulses for pacing the heart.

4. The pulse generator device of claim 1 wherein the pulse circuit is capable of generating high voltage pulses to halt tachyarrhythmia conditions in the heart.

5. The pulse generator device of claim 4 further comprising a second switch operable to disconnect the sense amplifier from the highpass filter.

6. The pulse generator device of claim 5 further comprising control means for operating the second switch to disconnect the sense amplifier from the highpass filter prior to an electrical pulse being generated by the pulse circuit.

7. The pulse generator device of claim 4 wherein the lowpass filter includes a capacitor coupled to the ground node.

8. The pulse generator device of claim 7 further comprising a second switch operable to effectively remove the capacitor from the lowpass filter.

9. The pulse generator device of claim 8 further comprising control means for operating the second switch to effectively remove the capacitor for a selected period of time ranging from before an electrical pulse is generated by the pulse circuit until after the electrical pulse dissipates.

10. The pulse generator device of claim 1 wherein the sense amplifier comprises a differential sense amplifier.

11. A cardiac pacemaker for generating electrical pacing pulses and coupleable to an electrode which senses electrical activity of the heart and carries the electrical pacing pulses to the heart, the cardiac pacemaker comprising:

input/output terminal connectable to the electrode to receive the sensed electrical activity of the heart from the electrode and provide the electrical pacing pulses to the electrode;

a bandpass filter coupled to the input/output terminal for filtering the sensed electrical activity, the bandpass filter including a resistive portion coupled to a ground node;

a switch operable to effectively remove the resistive portion from the bandpass filter;

a sense amplifier coupled to the bandpass filter for amplifying the electrical activity of the heart passed from the bandpass filter;

a cardiac depolarization detector coupled to the sense amplifier for detecting depolarizations in the amplified electrical activity of the heart and providing a depolarization signal indicative of the depolarizations; and a pulse circuit coupled to the input/output terminal and the cardiac depolarization detector for generating the electrical pacing pulses based on the depolarization signal.

12. The cardiac pacemaker of claim 11 further comprising control means for operating the switch to effectively remove the resistive portion for a selected period of time following each electrical pacing pulse generated by the pulse circuit.

13. The cardiac pacemaker of claim 11 wherein the bandpass filter includes:

a lowpass filter coupled to the input/output terminal for filtering the sensed electrical activity and the electrical pacing pulses; and a highpass filter coupled to the lowpass filter and the sense amplifier for further filtering the electrical activity passed from the lowpass filter, the highpass filter including the resistive portion.

14. A cardioverter/defibrillator with pacing capability for generating electrical pulses including shock pulses and pacing pulses and coupleable to an electrode which senses electrical activity of the heart and carries the electrical pulses to the heart, the cardioverter/defibrillator comprising:

an input/output terminal connectable to the electrode to receive the sensed electrical activity of the heart from the electrode and provide the electrical pulses to the electrode;

a bandpass filter coupled to the input/output terminal for filtering the sensed electrical activity, the bandpass filter including a resistive portion coupled to a ground node;

a first switch operable to effectively remove the resistive portion from the bandpass filter;

a sense amplifier coupled to the bandpass filter for amplifying the electrical activity of the heart passed from the bandpass filter;

a second switch operable to disconnect the sense amplifier from the bandpass filter;

a cardiac depolarization detector coupled to the sense amplifier for detecting depolarizations in the amplified electrical activity of the heart and providing a depolarization signal indicative of the depolarizations;

a shock pulse circuit coupled to the input/output terminal and the cardiac depolarization detector for generating the shock pulses based on the depolarization signal; and a pace pulse circuit coupled to the input/output terminal and the cardiac depolarization detector for generating the pacing pulses based on the depolarization signal.

15. The cardioverter/defibrillator of claim 14 further comprising control means for operating the first switch to effectively remove the resistive portion for a selected period of time following each electrical pulse.

16. The cardioverter/defibrillator of claim 14 further comprising control means for operating the second switch to disconnect the sense amplifier from the bandpass filter prior to each shock pulse being generated by the shock pulse circuit.

17. The cardioverter/defibrillator of claim 16 wherein the control means further operates the second switch to connect the sense amplifier to the bandpass filter when each pacing pulse is being generated by the pace pulse circuit.

18. The cardioverter/defibrillator of claim 14 wherein the bandpass filter includes:

a lowpass filter coupled to the input/output terminal for filtering the sensed electrical activity; and a highpass filter coupled to the lowpass filter and the sense amplifier for further filtering the electrical activity passed from the lowpass filter, the highpass filter including the resistive portion.

19. The cardioverter/defibrillator of claim 18 wherein the lowpass filter includes a capacitor coupled to the ground node.

20. The cardioverter/defibrillator of claim 19 further comprising a third switch operable to effectively remove the capacitor from the lowpass filter.

21. The cardioverter/defibrillator of claim 20 further comprising control means for operating the third switch to effectively remove the capacitor for a selected period of time ranging from before each shock pulse is generated by the shock pulse circuit until after each shock pulse dissipates.

22. The cardioverter/defibrillator of claim 21 wherein the control means further operates the third switch to keep the capacitor in the lowpass filter when each pacing pulse is being generated by the pace pulse circuit.

23. An apparatus for effectively removing the after potential occurring after a shock pulse is delivered in a cardioverter/defibrillator system having an electrode for sensing electrical activity of the heart and carrying the shock pulse to the heart and a sense amplifier for detecting the electrical activity from the electrode, the system comprising:

switch means for disconnecting the sense amplifier from the electrode during the delivery of the shock pulse;

a lowpass filter coupled to the electrode and having filter components including a capacitive component for filtering the sensed electrical activity;

a highpass filter coupled to the lowpass filter and the sense amplifier and having filter components for further filtering the electrical activity passed from the lowpass filter;

clamping means for limiting a charge in the capacitive component of the lowpass filter resulting from the after potential; and equilibrium means for allowing the filter components of the lowpass filter and the highpass filter to return to an equilibrium state following the delivery of the shock pulse.

24. The apparatus of claim 23 wherein the filter components of the highpass filter include a resistive component coupled to a ground node, and wherein the equilibrium means operates to effectively remove the resistive component from the highpass filter for a selected period of time following the delivery of the shock pulse.

25. The apparatus of claim 23 wherein the cardioverter/defibrillator system includes pacing means for generating pacing pulses and the electrode further carries the pacing pulses to the heart, wherein the apparatus effectively removes the after potential occurring after each pacing pulse is delivered by the pacing means, wherein the switch means couples the sense amplifier to the electrode during the delivery of each pacing pulse, but the equilibrium means couples the second amplifier to a ground node during the delivery of each pacing pulse and the equilibrium means allows the filter components of the lowpass filter and the highpass filter to return to an equilibrium state following the delivery of each pacing pulse.

26. The apparatus of claim 25 wherein the filter components of the highpass filter include a resistive component coupled to a ground node, and wherein the equilibrium means operates to effectively remove the resistive component from the highpass filter for a selected period of time following the delivery of each pacing pulse.

27. The apparatus of claim 23 wherein the capacitive component of the lowpass filter is coupled to a ground node, and wherein the clamping means includes means for effectively removing the capacitive component for a selected period of time ranging from before a shock pulse is delivered until after the shock pulse dissipates.

28. The apparatus of claim 23 wherein the filter components of the lowpass filter further include a resistive component having a first terminal coupled to the electrode and a second terminal coupled to the highpass filter, and wherein the capacitive component has a first terminal coupled to the second terminal of the resistive component and the highpass filter and a second terminal coupled to a ground node.

29. The apparatus of claim 28 wherein the clamping means includes shorting means for connecting the second terminal of the resistive component to the ground node for a selected period of time ranging from before a shock pulse is delivered until after the shock pulse dissipates.

30. The apparatus of claim 23 wherein the filter components of the highpass filter include:

a capacitive component having a first terminal coupled to the lowpass filter and a second terminal coupled to the sense amplifier; and a resistive component having a first terminal coupled to the second terminal of the capacitive component and the sense amplifier and a second terminal coupled to a ground node.

31. The apparatus of claim 30 wherein the equilibrium means includes shorting means for connecting the second terminal of the capacitive component to the ground node for a selected period of time following the delivery of the shock pulse.

32. The apparatus of claim 30 wherein the cardioverter/defibrillator system includes pacing means for generating pacing pulses and the electrode further carries the pacing pulses to the heart, and wherein the equilibrium means includes shorting means for connecting the second terminal of the capacitive component to the ground node for a selected period of time following the delivery of a pacing pulse.

33. The apparatus of claim 23 wherein the clamping means includes means for bypassing through a ground node a shock current created by the delivery of the shock pulse.

34. An apparatus for effectively removing the after potential occurring after a pace pulse is delivered in a cardiac pacemaker system having an electrode for sensing electrical activity of the heart and carrying the pace pulse to the heart and a sense amplifier for detecting the electrical activity from the electrode, the apparatus comprising:

a lowpass filter coupled to the electrode and having filter components for filtering the sensed electrical activity and the pace pulse;

a highpass filter coupled to the lowpass filter and the sense amplifier and having filter components for further filtering the electrical activity passed from the lowpass filter; and equilibrium means for allowing the filter components of the lowpass filter and the highpass filter to return to an equilibrium state following the delivery of the pace pulse.

35. The apparatus of claim 34 wherein the filter components of the highpass filter include a resistive component coupled to a ground node, and wherein the equilibrium means operates to effectively remove the resistive component from the highpass filter for a selected period of time following the delivery of the pacing pulse.

36. The apparatus of claim 34 wherein the filter components of the lowpass filter include:

a resistive component having a first terminal coupled to the electrode and a second terminal coupled to the highpass filter; and a capacitive component having a first terminal coupled to the second terminal of the resistive component and the highpass filter and a second terminal coupled to a ground node.

37. The apparatus of claim 34 wherein the filter components of the highpass filter include:

a capacitive component having a first terminal coupled to the lowpass filter and a second terminal coupled to the sense amplifier; and a resistive component having a first terminal coupled to the second terminal of the capacitive component and the sense amplifier and a second terminal coupled to a ground node.

38. The apparatus of claim 37 wherein the equilibrium means includes shorting means for connecting the second terminal of the capacitive component to the ground node for a selected period of time following the delivery of the pacing pulse.

39. A method of effectively removing the after potential occurring after a shock pulse is delivered in a cardioverter/defibrillator system including an electrode for sensing electrical activity of the heart and for carrying the shock pulse to the heart, and including a sense amplifier for detecting the electrical activity from the electrode, the sensed electrical activity having a plurality of signal components, each signal component having a distinct frequency in a range of relatively high and low frequencies, the method comprising the steps of:

disconnecting the sense amplifier from the electrode during the delivery of the shock pulse;

bypassing through a ground node a shock current created by the delivery of the shock pulse;

filtering, with at least one first filter component, signal components of relatively high frequency from the sensed electrical activity;

filtering, with at least one second filter component, signal components of relatively low frequency from the filtered electrical activity; and allowing the at least one first filter component and the at least one second filter component to return to an equilibrium state following the delivery of the shock pulse.

40. The method of claim 39 wherein the cardioverter/defibrillator system includes pacing circuitry for generating pacing pulses and the electrode further carries the pacing pulses to the heart, wherein the method further performs the step of effectively removing the after potential occurring after each pacing pulse is delivered by further comprising the steps of:

connecting the sense amplifier to the electrode and a ground node during the delivery of the pacing pulse; and allowing the at least one first filter component and the at least one second filter component to return to an equilibrium state following the delivery of the pacing pulse.

41. A cardiac rhythm management system comprising:

an electrode for sensing electrical activity of the heart and carrying electrical pulses to the heart;

a lowpass filter coupled to the electrode for filtering the sensed electrical activity;

a highpass filter coupled to the lowpass filter for further filtering the electrical activity passed from the lowpass filter, the highpass filter including a resistive portion coupled to a ground node;

a switch operable to effectively remove the resistive portion from the highpass filter;

a sense amplifier coupled to the highpass filter for amplifying the electrical activity of the heart passed from the highpass filter;

a cardiac depolarization detector coupled to the sense amplifier for detecting depolarizations in the amplified electrical activity of the heart and providing a depolarization signal indicative of the depolarizations; and pulse circuit coupled to the electrode and the cardiac depolarization detector for providing the electrical pulses to the electrode based on the depolarization signal.

42. The cardiac rhythm management system of claim 41 further comprising control means for operating the switch to effectively remove the resistive portion for a selected period of time following each electrical pulse provided by the pulse circuit.

43. The cardiac rhythm management system of claim 42 wherein the control means comprises a microprocessor.

* * * * *